(12) United States Patent
Levin

(10) Patent No.: US 7,996,085 B2
(45) Date of Patent: Aug. 9, 2011

(54) ISOLATION OF SENSING CIRCUIT FROM PACE GENERATOR

(75) Inventor: Michael Levin, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 105 days.

(21) Appl. No.: 12/478,171

(22) Filed: Jun. 4, 2009

(65) Prior Publication Data

US 2010/0121393 A1    May 13, 2010

Related U.S. Application Data

(60) Provisional application No. 61/113,729, filed on Nov. 12, 2008.

(51) Int. Cl.
*A61N 1/00* (2006.01)
(52) U.S. Cl. .................................................. 607/9
(58) Field of Classification Search .................. 607/9
See application file for complete search history.

(56) References Cited

U.S. PATENT DOCUMENTS

| 4,158,863 | A | 6/1979 | Naylor |
| 5,983,126 | A | 11/1999 | Wittkampf |
| 6,226,542 | B1 | 5/2001 | Reisfeld |
| 6,301,496 | B1 | 10/2001 | Reisfeld |
| 6,814,733 | B2 | 11/2004 | Schwartz et al. |
| 2006/0173251 | A1 | 8/2006 | Govari et al. |
| 2006/0271119 | A1* | 11/2006 | Ni et al. .................. 607/9 |
| 2007/0038078 | A1 | 2/2007 | Osadchy |

FOREIGN PATENT DOCUMENTS

| EP | 1 679 034 A1 | 7/2006 |
| WO | 00/61008 A1 | 10/2000 |

OTHER PUBLICATIONS

EP Search Report 09 25 2594 Dated Jan. 27, 2010.

* cited by examiner

*Primary Examiner* — George Manuel
(74) *Attorney, Agent, or Firm* — Louis J. Capezzuto

(57) ABSTRACT

In a system for sensing electrical signals within a living body, and specifically for tracking location of an object in the body using impedance measurements, an isolation circuit maintains isolation between the pacing and position sensing circuits, even while the heart is being paced.

13 Claims, 4 Drawing Sheets under development of the present invention. It will be apparent
ISOLATION OF SENSING CIRCUIT FROM PACE GENERATOR

CROSS-REFERENCE TO RELATED APPLICATIONS

This Application claims the benefit of U.S. Provisional Application No. 61/113,729 filed on Nov. 12, 2008, which is herein incorporated by reference.

BACKGROUND OF THE INVENTION

1. Field of the Invention

This invention relates to sensing of electrical signals within a living body. More particularly, this invention relates to sensing of electrical signals within a living body, while tracking an object in the body using impedance measurements.

2. Description of the Related Art

A wide range of medical procedures involve placing objects, such as sensors, tubes, catheters, dispensing devices, and implants, within the body. Position sensing systems have been developed for tracking such objects. For example, U.S. Pat. No. 5,983,126, to Wittkampf, whose disclosure is incorporated herein by reference, describes a system in which catheter position is detected using electrical impedance methods. U.S. Patent Application Publications 2006/0173251, to Govari et al., and 2007/0038078, to Osadchy, which are herein incorporated by reference, describe impedance-based methods for sensing the position of a probe by passing electrical currents through the body between an electrode on the probe and a plurality of locations on a surface of the body.

Systems such as those described above may be used to track the position of a catheter within a patient's heart. A physician may use the catheter, for example, for diagnostic purposes, such as electrophysiology studies, and for therapeutic purposes, such as treating cardiac arrhythmias. In the course of such procedures, the physician may wish to pace the heart, by applying a suitable electrical signal via an electrode at or near the catheter tip. For this purpose, it is common to connect a pacing generator across the same electrodes on the catheter as are used for impedance-based position sensing.

SUMMARY OF THE INVENTION

For accurate position measurement using impedance-based techniques, it is desirable that electrical currents flow between the electrodes on the catheter and the body surface electrodes without leakage to other current sinks. Pacing generators, however, typically have low input impedance, and therefore, when a pacing generator is connected across the catheter electrodes, it will tend to short-circuit the signals that are used in impedance-based position sensing. Embodiments of the present invention provide a simple, novel type of circuit that can be used to maintain isolation between the pacing and impedance-based position sensing circuits, even while the heart is being paced.

An embodiment of the invention provides a medical apparatus, including a probe having one or more electrodes thereon, adapted for insertion into a heart of a subject. The apparatus includes a position sensing circuit coupled to the electrodes, a pacing generator for producing electrical pacing signals to electrically activate the heart, and a coupling element, which is inserted between the pacing generator and the electrodes and the position sensing circuit and is characterized by a relatively high first impedance at a voltage that is within a predetermined range and a second impedance that is low relative to the first impedance when the voltage is without the predetermined range.

According to one aspect of the apparatus, the coupling element includes a pair of diodes of opposing polarities connected in parallel.

According to an additional aspect of the apparatus, the coupling element includes two bipolar junction transistors connected in parallel.

According to still another aspect of the apparatus, the pacing generator has first and second output leads and the coupling element includes first and second cross-diode pairs connected to the first and second output leads, respectively.

The predetermined range may be −0.7 to +0.7 volts.

The apparatus may include a router coupled to the pacing generator for directing an output of the pacing generator to selected ones of the electrodes, wherein the position sensing circuit and the pacing generator are simultaneously electrically connected to the selected ones of the electrodes.

The apparatus may include electrocardiographic circuitry coupled to the electrodes and concurrently coupled to the pacing generator via the coupling element.

Other embodiments of the invention provide methods for carrying out the invention.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Architecture

Figure 1:
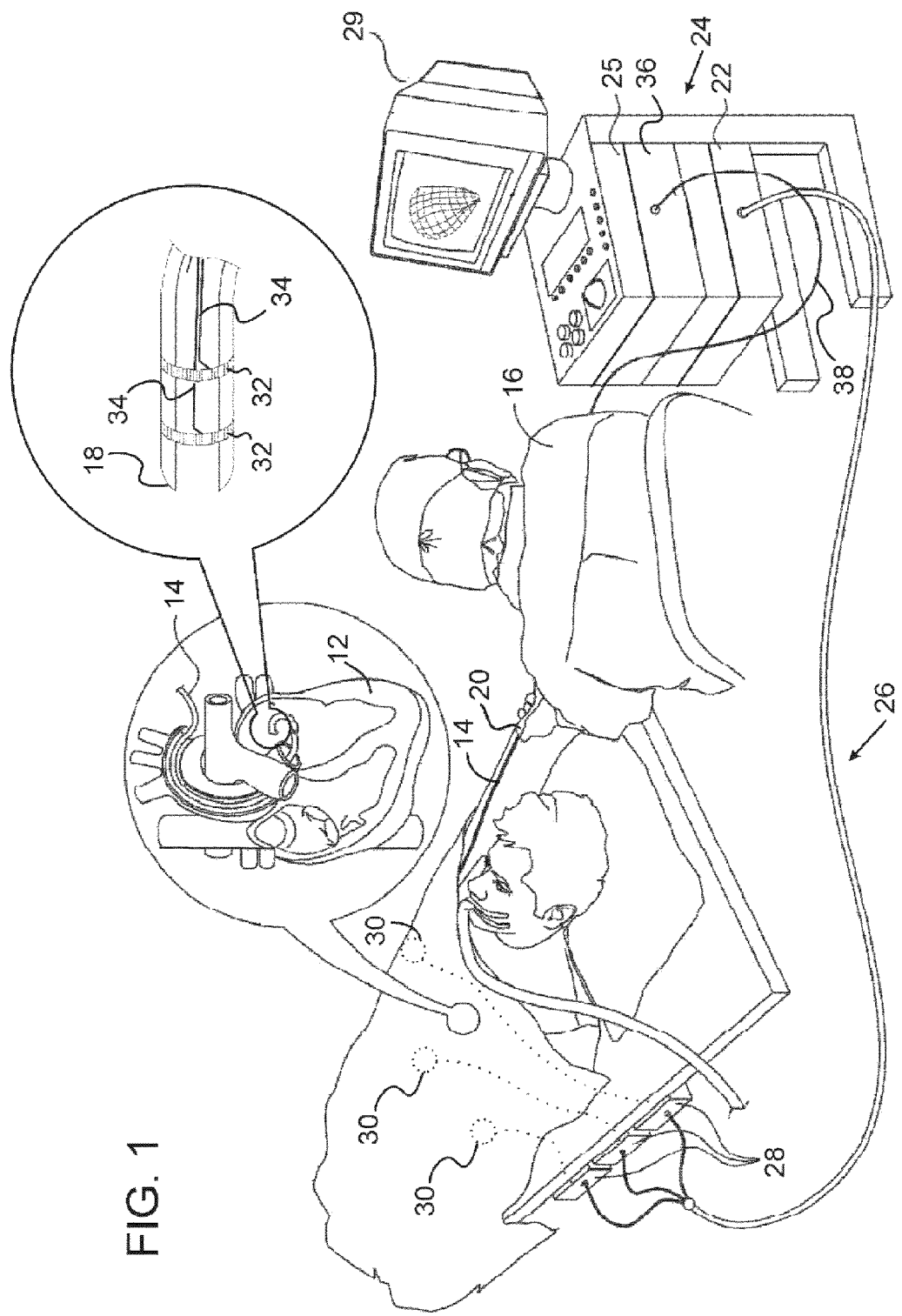
FIG. 1 is a pictorial illustration of a system for detecting areas of abnormal electrical activity and performing ablative procedures on a heart of a living subject in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject in accordance with a disclosed embodiment of the invention. A probe or catheter 14 is a component of the system 10, and is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

Electrical signals can be conveyed from the heart 12 through one or more electrodes 32 located at or near the distal tip 18 of the catheter 14 and through wires 34 to a console 24. Pacing signals and other control signals areas may be conveyed from the console 24 through the wires 34 and the electrodes 32 to the heart 12. The electrodes 32 also function as components of an impedance-based positioning system 26 for locating the catheter. Additional wire connections 28 link the console 24 with body surface electrodes 30 and other components of the positioning system 26. Further details of the positioning system 26 are presented below.

Additionally, areas determined to be abnormal by evaluation of the electrical activation maps can be ablated by application of thermal energy, e.g., by passage of radiofrequency electrical current through wires 34 in the catheter to the electrodes 32, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired for the ablation. A positioning processor 22 is an element of an impedance-based positioning system 26 that measures location and orientation coordinates of the catheter 14.

The console 24 contains a pacing generator 25, the output of which is connected to one or more electrodes 32 on the outer surface of the catheter 14 by wires 34. The electrodes 32 are at least dual-purpose, being employed to conduct first electrical signals from the heart 12 to the positioning processor 22 and second electrical signals from the pacing generator 25 to the heart 12. In some embodiments, the operator 16 may cause third electrical signals, containing ablative radiofrequency energy to be conducted to the electrodes 32 from an ablation power generator 36, which can be incorporated in the console 24. Such techniques are disclosed in commonly assigned U.S. Pat. No. 6,814,733, which is herein incorporated by reference.

As noted above, the catheter 14 is coupled to the console 24, which enables the operator 16 to observe and regulate the functions of the catheter 14. The positioning processor 22 is preferably a computer with appropriate signal processing circuitry. The processor is coupled to drive a display monitor 29. The signal processing circuits typically receive, amplify, filter and digitize signals from the catheter 14, including signals conveyed via the electrodes 32. The digitized signals are received and analyzed in the console 24 to derive electroanatomical information of medical interest. The information derived from this analysis is used to generate an electrophysiological map of at least a portion of the heart 12 or related structures such as the pulmonary venous ostia. The map may be employed for diagnostic purposes, such as locating an arrhythmogenic area in the heart, or to facilitate therapeutic ablation.

Other signals used by the positioning system 26 are transmitted from the console 24 through the wires 34 and the electrodes 32 in order to compute the position and orientation of the catheter 14.

Typically, the system 10 includes other elements. For example, the console 24 may include an electrocardiographic device 38, coupled to receive signals from one or more body surface electrodes, so as to provide an ECG synchronization signal to the console 24, which may be displayed on the display monitor 29 or on a separate display (not shown). The system 10 typically also includes a reference position sensor, either on an externally-applied reference electrode attached to the exterior of the subject's body, or on another internally-placed reference catheter (not shown), which is inserted into the heart 12 and maintained in a fixed position relative to the heart 12. By comparing the position of the catheter 14 to that of the reference catheter, the coordinates of catheter 14 are accurately determined relative to the heart 12, irrespective of heart motion. Alternatively, any other suitable method may be used to compensate for heart motion.

Figure 2:
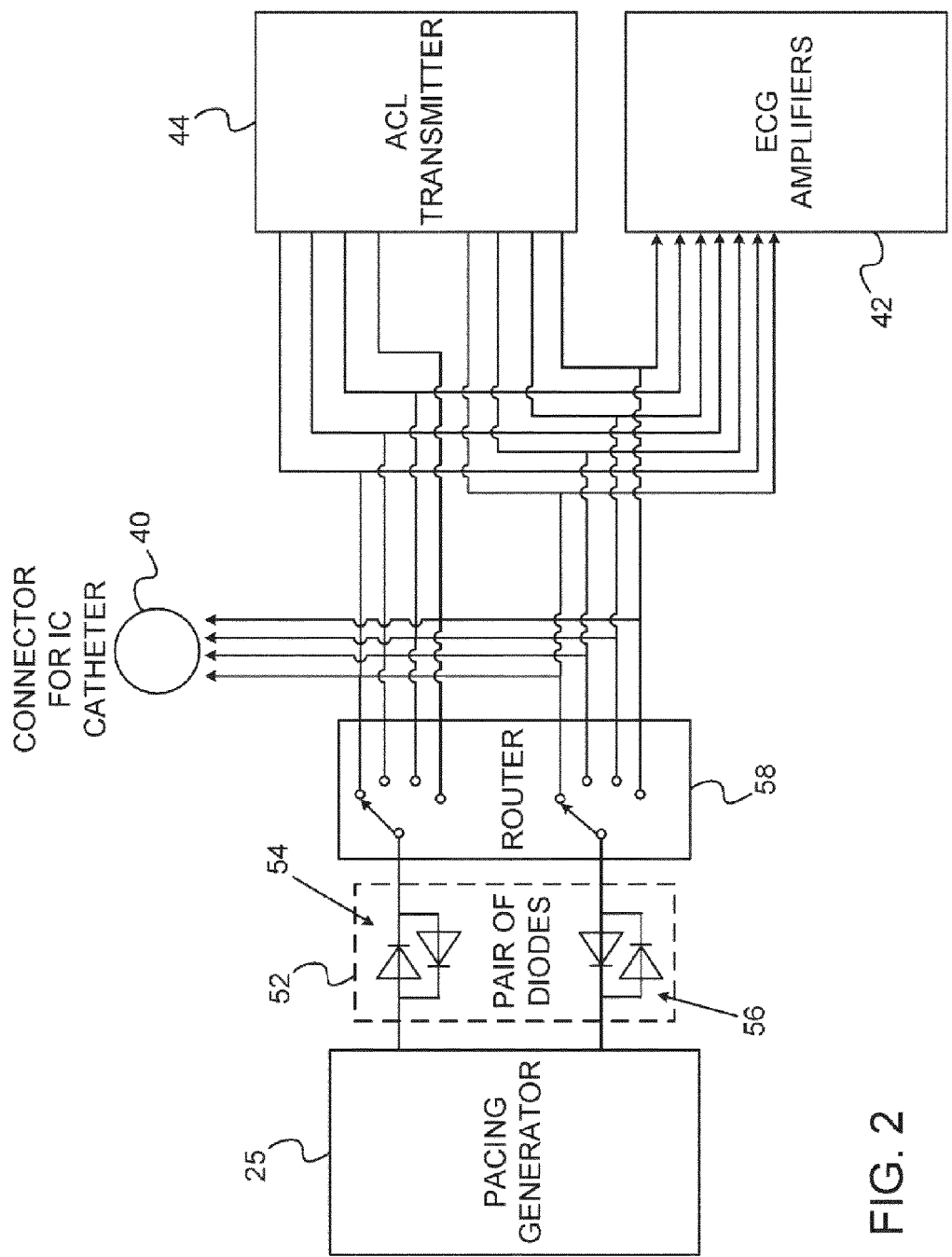
FIG. 2 is a schematic diagram showing electrical connections between catheter-mounted electrodes and other components of the system shown in FIG. 1 in accordance with a disclosed embodiment of the invention.

Reference is now made to FIG. 2, which is a schematic diagram showing electrical connections between the electrodes 32 on the catheter 14 via a coupling adapter 40, and other components of the system 10 (FIG. 1), in accordance with a disclosed embodiment of the invention. FIG. 2 includes ECG amplifiers 42, which are components of the electrocardiographic device 38 (FIG. 1). More particularly, FIG. 2 illustrates how the pacing generator 25, ECG amplifiers 42, and impedance-based position sensing circuitry 44 may be electrically connected simultaneously to the electrodes 32. The position sensing circuitry 44 is referred to in the figure as an accurate current location (ACL) transmitter, and operates in a manner similar to that described in the above-mentioned publication by Osadchy. Its outputs are linked to the positioning processor 22 (FIG. 1).

Figure 3:
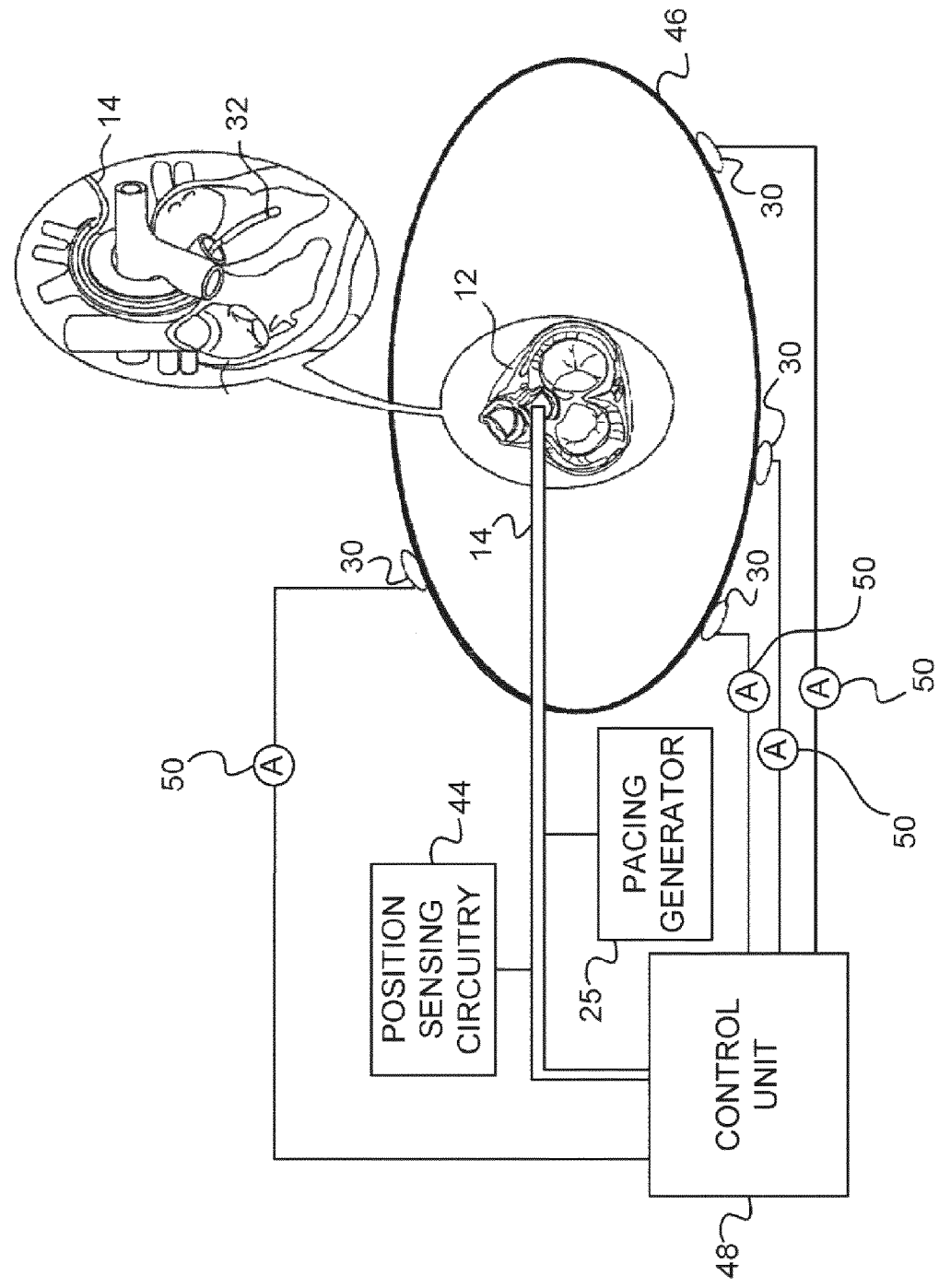
FIG. 3 schematically illustrates an impedance-based position measuring system as a component of the system shown in FIG. 1, in accordance with a disclosed embodiment of the invention.

Reference is now made to FIG. 3, which is a schematic illustration of an impedance-based position measuring system as a component of the system 10 (FIG. 1), in accordance with a disclosed embodiment of the invention. The pacing generator 25 and position sensing circuitry 44 are connected to the catheter 14 as described above with reference to FIG. 2. A plurality of body surface electrodes 30, which can be adhesive skin patches, are coupled to a body surface 46 (e.g., the skin) of the subject. The body surface electrodes 30 may be placed at any convenient locations on the body surface 46 in the vicinity of the site of the medical procedure. Typically, the locations of the body surface electrodes 30 are spaced apart. For example, for cardiac applications, the body surface electrodes 30 are typically placed around the subject's chest. A control unit 48, normally disposed in the console 24 (FIG. 1) drives a current between one or more of the electrodes 32 and one or more of the body surface electrodes 30. Currents through the body surface electrodes 30 are measured by respective current measurement circuits 50. The current measurement circuits 50 are typically configured to be affixed to a body surface patch, or, alternatively, may be situated within the console 24 (FIG. 1).

Reverting to FIG. 2, the pacing generator 25 is connected to the catheter electrodes 32 via a coupling element 52 comprising cross-diodes 54, 56. In this configuration, each of the cross-diodes 54, 56 comprises a pair of diodes coupled in parallel and having opposing polarities. The pacing generator 25 sees an open circuit for low-voltage signals (in the range between about a range of −0.7 to +0.7 V and a low impedance at voltages outside this range). Table 1 presents the impedance in Ohms of two general purpose diodes, BAS16 and BAV99, as a function of the forward voltage. Both of these diodes, which have a fast response, are suitable for the cross diodes 54, 56.

TABLE 1

| Voltage | Diode BAS16 impedance | Diode BAV99 impedance |
|---|---|---|
| 0.1 | 3333333 | 5555556 |
| 0.2 | 833333 | 1333333 |
| 0.3 | 176471 | 272727 |
| 0.4 | 36364 | 50000 |
| 0.5 | 6250 | 7463 |
| 0.6 | 1017 | 1000 |
| 0.7 | 171 | 163 |
| 0.8 | 33 | 31 |
| 0.9 | 10 | 11 |
| 1 | 5 | 7 |
| 1.1 | 3 | 4 |
| 1.2 | 2 | 4 |
| 1.3 | 2 | 3 |

Thus, the relatively high-voltage pacing signals produced by the pacing generator 25 are not significantly impeded by the cross-diodes 54, 56. Low-voltage position sensing signals that are output by the position sensing circuitry 44, however, pass directly to the catheter 14 through a router 58 and the adapter 40 without significant leakage into the pacing generator 25. In embodiments in which the catheter 14 has a plurality of electrodes 32 (FIG. 1), the router 58 directs pacing signals to selected sets of the electrodes. Irrespective of the router-directed output of the pacing generator 25, the pacing generator 25, ECG amplifiers 42 and position sensing circuitry 44 may be simultaneously operational via the electrodes 32 of the catheter 14.

Alternate Embodiment

Although the embodiment shown in FIG. 2 uses pairs of diodes to isolate the position sensing circuit from the pacing generator, other types of coupling elements with suitable non-linear V-I (voltage-current) dependence and symmetrical bidirectional conductivity may similarly be used for this purpose, for example, circuits including transistors. Such coupling elements should be characterized generally by high impedance at low voltage and a drop in impedance when the voltage reaches a certain threshold value.

Figure 4:
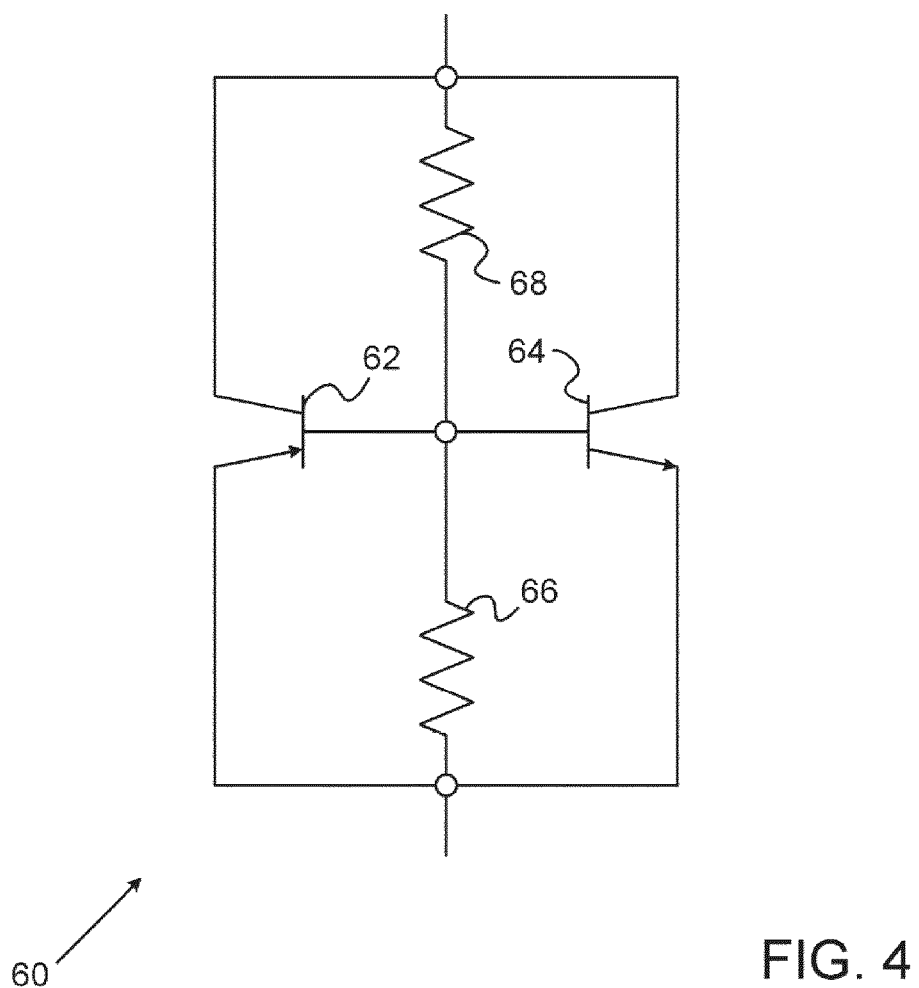
FIG. 4 is an electrical schematic of a circuit that is suitable for use as a coupling element in the arrangement shown in FIG. 2, in accordance with an alternate embodiment of the invention.

Reference is now made to FIG. 4, which is an exemplary electrical schematic of a circuit 60 suitable for use as the coupling element 52 (FIG. 2), in accordance with an alternate embodiment of the invention. The circuit 60 comprises a pair of bipolar junction transistors, a PNP (Positive-Negative-Positive) transistor 62 and NPN (Negative-Positive-Negative) transistor 64 and two resistors, Resistor 66 has a non-critical value in the range of a few thousand Ohms. Resistor 68 should be a few hundred ohms. General purpose transistors 2N2222 and 2N2907 are suitable for the two transistors.

Operation

Referring again to FIG. 1, to use the system 10, the catheter 14 is conventionally introduced into the heart 12, and navigated into an operating position, all the while receiving position signals from the electrodes in the position sensing circuitry 44 (FIG. 2) and analyzing the position signals in the positioning processor 22. The pacing generator 25 is activated, either continuously or intermittently, according to the requirements of the medical procedure. By suitably controlling the router 58, the signals of the pacing generator 25 may be selectively directed to different sets of the electrodes 32. The position sensing circuitry 44 continues to operate and receive new signals even while the pacing generator 25 is active and connected to common electrodes with the position sensing circuitry 44.

Eventually, if the medical procedure is successful, or otherwise terminates, the pacing generator 25, and optionally the position sensing circuitry 44 (FIG. 2) are disabled, and the catheter 14 is withdrawn.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A medical apparatus, comprising:
a probe having one or more electrodes thereon, for insertion into a heart of a subject;
a position sensing circuit, coupled to the electrodes;
a pacing generator for producing electrical pacing signals to electrically activate the heart; and
a coupling element, which is coupled between the pacing generator and the electrodes and the position sensing circuit and is characterized by a relatively high first impedance at a voltage that is within a predetermined range and a second impedance that is low relative to the first impedance when the voltage is without the predetermined range.

2. The apparatus according to claim 1, wherein the coupling element comprises a pair of diodes of opposing polarities connected in parallel.

3. The apparatus according to claim 1, wherein the coupling element comprises two bipolar junction transistors connected in parallel.

4. The apparatus according to claim 1, wherein the pacing generator has first and second output leads and the coupling element comprises first and second cross-diode pairs connected to the first and second output leads, respectively.

5. The apparatus according to claim 1, wherein the predetermined range is −0.7 to +0.7 volts.

6. The apparatus according to claim 1, wherein the electrodes comprise a plurality of electrodes, further comprising:
a router coupled to the pacing generator for directing an output of the pacing generator to selected ones of the electrodes, wherein the position sensing circuit and the pacing generator are simultaneously electrically connected to the selected ones of the electrodes.

7. The apparatus according to claim 1, further comprising electrocardiographic circuitry coupled to the electrodes and concurrently coupled to the pacing generator via the coupling element.

8. A method of cardiac catheterization, comprising the steps of:
inserting a probe into a heart of a living subject; the probe having one or more electrodes disposed thereon;
connecting the electrodes to a position sensing circuit and a pacing generator;
isolating the pacing generator from the position sensing circuit using a coupling element, which is coupled between the pacing generator and the electrodes and the position sensing circuit and is characterized by a relatively high first impedance at a voltage that is within a predetermined range and a second impedance that is low relative to the first impedance when the voltage is without the predetermined range; and operating the pacing generator to transmit pacing signals to the electrodes to electrically activate the heart while simultaneously receiving position signals in the position sensing circuit from the electrodes.

9. The method according to claim 8, wherein the coupling element comprises a pair of diodes of opposing polarities connected in parallel.

10. The method according to claim 8, wherein the coupling element comprises two bipolar junction transistors connected in parallel.

11. The method according to claim 8, wherein the pacing generator has first and second output leads and the coupling element comprises first and second cross-diode pairs, further comprising connecting the first and second cross-diode pairs to the first and second output leads, respectively.

12. The method according to claim 8, wherein the predetermined range is −0.7 to +0.7 volts.

13. The method according to claim 8, wherein the electrodes comprise a plurality of electrodes, further comprising the step of directing an output of the pacing generator to selected ones of the electrodes while the position sensing circuit and the pacing generator are activated and are simultaneously electrically connected to the selected ones of the electrodes.

\* \* \* \* \*